(12) United States Patent
Dow et al.

(10) Patent No.: US 7,300,669 B2
(45) Date of Patent: Nov. 27, 2007

(54) FLUTICASONE LOTION HAVING IMPROVED VASOCONSTRICTOR ACTIVITY

(75) Inventors: Gordon J. Dow, Petaluma, CA (US); Keith Arthur Johnson, Durham, NC (US); Frances Furr Kelly, Durham, NC (US); Robert William Lathrop, Fort Collins, CO (US); Rukmini Rajagopalan, Durham, NC (US)

(73) Assignee: Altana Inc., Melville, NY (US)

( * ) Notice: Subject to any disclaimer, the term of this patent is extended or adjusted under 35 U.S.C. 154(b) by 530 days.

(21) Appl. No.: 10/800,840

(22) Filed: Mar. 15, 2004

(65) Prior Publication Data

US 2004/0176342 A1  Sep. 9, 2004

Related U.S. Application Data

(63) Continuation of application No. 09/830,037, filed as application No. PCT/GB99/03472 on Oct. 20, 1999, now abandoned.

(51) Int. Cl.
*A61K 9/14* (2006.01)
*A61K 31/56* (2006.01)

(52) U.S. Cl. ............... 424/484; 424/485; 424/486; 514/177

(58) Field of Classification Search ............ 514/177; 424/484, 485, 486
See application file for complete search history.

(56) References Cited

U.S. PATENT DOCUMENTS 4,985,418 A * 1/1991 Richards

FOREIGN PATENT DOCUMENTS

| EP | 0042827 | 12/1981 |
| WO | WO-9214472 | 9/1992 |
| WO | WO9214472 | 9/1992 |

OTHER PUBLICATIONS

Gordon, Clinical Therapeutics, Feb. 1998; 20(1):26-39.*
Budavari, Merck Index 11th ed. 1989, monograph 6021 and 7879.*
Bleehen, S. S. et al: British Journal of Dermatology, vol. 133, No. 4, 1995, pp. 592-597.
Spencer, Caroline M et al: Biodrugs, vol. 7, No. 4, 1997, pp. 318-334.
"Physicians' Desk Reference monographs", 7 pages.
"Potency Ranking of Some Commonly Used Topical Corticosteroids", *Temovate literature*, 1 page.
Bleehan, S S., et al., "Fluticasone propionate 0.05% cream in the treatment of atopic eczema: a multicentre study comparing once-daily treatment and once-daily vehicle cream application versus twice-daily treatment.", *British Journal of Dermatology*, 133(4), (1995),592-597.
Budavari, Susan , et al., "Monographs 6021 and 7879", *Merck Index 11th ed.*, Rahway, N.J. : Merck,(1989).
Cornell, Roger C., et al., "Potency Ranking of Some Commonly Used Topical Steroids", *Topical Corticosteroids—Guidelines for Therapy Hoechst-Roussel Pharmaceuticals Inc.*, (1985),24-25.
Gordon, M. L., "The role of clobetasol propionate emollient 0.05% in the treatment of patients with dry, scaly, corticosteroid-responsive dermatoses.", *Clinical Therapeutics*, 20(1), (Feb. 1998),26-39.
Spencer, Caroline M., "Topical Fluticasone Propionate: A review of its pharmacological properties and therapeutic use in the treatment of dermatological disorders", *Biodrugs*, 7(4), (1997),318-334.

* cited by examiner

*Primary Examiner*—San-Ming Hui
(74) *Attorney, Agent, or Firm*—Schwegman, Lundberg & Woessner, P.A.

(57) ABSTRACT

A fluticasone lotion having improved vasoconstrictor and anti-inflammatory activity and higher than expected potency. The fluticasone lotion contains 0.05 weight percent fluticasone propionate and an oil-in-water vehicle that includes excipients. The fluticasone lotion is unexpectedly efficacious while exhibiting an improved safety profile.

19 Claims, No Drawings

FLUTICASONE LOTION HAVING IMPROVED VASOCONSTRICTOR ACTIVITY

This application is a continuation of U.S. Ser. No. 09/830,037 filed 20 Apr. 2001, now abandoned which is a §371 national stage filing of PCT/GB99/03472 filed 20 Oct. 1999.

FIELD OF THE INVENTION

The present invention is generally directed to a lotion comprising fluticasone.

BACKGROUND OF THE INVENTION

Fluticasone propionate is a steroid having anti-inflammatory, anti-pruitic, and vasoconstrictive properties. Fluticasone propionate cream (0.05%) is sold under the tradename CUTIVATE® cream. Each gram of CUTIVATE® cream (0.05%) contains 0.5 mg fluticasone propionate in a base of propylene glycol, mineral oil, cetostearyl alcohol, ceteth-20, isopropyl myristate, buffers and preservatives.

Mineral oil is a known occlusive agent. Occlusion in topical drug delivery is known to increase the vasoconstrictor potency of the topical steroid. By increasing the vasoconstrictor potency, the effectiveness of the steroid is increased. However, occlusive agents such as mineral oil can reduce the aesthetic appeal of topical formulations as they may impart an undesirable oily feel to the skin. By removing or significantly reducing the concentration of the occlusive agent, a decrease in the vasoconstrictor potency of the steroid would be expected. Thus, the effectiveness of the topical steroid formulation would be decreased.

The present fluticasone lotion invention unexpectedly shows increased vasoconstrictor potency of fluticasone at decreased concentrations of occlusive agent, thus increasing the steroid effectiveness. The instant fluticasone lotion also significantly improves the organoleptic feel and spreadability of the drug over a large area as compared to a cream. Specifically, the instant fluticasone lotion has improved vasoconstrictor activity over fluticasone cream formulations. The fluticasone lotion is systemically safe and exhibits significant vasoconstrictor potency and efficacy and excellent anti-inflammatory activity.

SUMMARY OF THE INVENTION

One aspect of the invention is a topical lotion comprising about 0.005 to 1.0 wt. % fluticasone, or a pharmaceutically acceptable salt or ester thereof; a thickening effective concentration of at least one thickener; a conditioning effective concentration of at least one skin conditioning agent; and, an emulsifying effective amount of a surfactant. Unless indicated otherwise herein, all percentages are in terms of weight percent (i.e., w/w, wt. %, etc.). Unless indicated otherwise herein, the term "about" is intended to include values, e.g., weight percents, proximate to the recited range that are equivalent in terms of the functionality of the individual ingredient, the composition or the invention. In addition, unless indicated otherwise herein, a recited range (e.g., weight percents or carbon groups) includes each specific value or identity within the range.

Another aspect of the present invention is a topical fluticasone lotion for the treatment of skin conditions (i.e., dermatological disorders). The lotion comprises about 0.005 to 1.0 wt. % fluticasone, or a pharmaceutically acceptable salt or ester thereof; about 1.0 to 10.0 wt. % of a $C_{14}$-$C_{20}$ fatty alcohol, or mixtures thereof; about 1.0 to 5.0 wt. % of at least one skin conditioning agent; about 5.0 to 15.0 wt. % of propylene glycol; up to about 10.0 wt. % mineral oil or soft white paraffin, and the balance being water. The lotion optionally contains additives such as preservatives and buffers.

Another aspect of the invention is a topical fluticasone lotion comprising fluticasone propionate in an amount of from about 0.005 to 1.0 wt. %; a $C_{14}$-$C_{20}$ fatty alcohol, or mixtures thereof, in an amount of from about 3.0 to 7.0 wt. %; at least one skin conditioning agent in an amount of from about 0.5 to 3.0 wt. %; at least one surfactant in an amount of about 0.25 to 3.0 wt. %; propylene glycol in an amount of from about 7.0 to 12.0 wt. %; up to about 10 wt. % mineral oil or soft white paraffin; and the balance in water, preferably purified water, USP.

Yet another aspect of the invention is a method of treating a skin condition. A skin condition (or dermatological disorder) includes, but is not limited to, corticosteroid-responsive dermatosis, atropic dermatitis, inflammation, eczema, erythema, papulation, scaling, erosion, oozing, crusting and pruritis. The method comprises the steps or acts of providing a lotion including about 0.005 to 1.0 wt. % fluticasone, or a pharmaceutically acceptable salt or ester thereof; about 1.0 to 10.0 wt. % of a $C_{14}$-$C_{20}$ fatty alcohol or mixtures thereof; about 1.0 to 5.0 wt. % of one or more skin conditioning agents; about 5.0 to 15.0 wt. % of propylene glycol; up to about 10.0 wt. % of mineral oil or white soft paraffin, and the balance in purified water; and, applying the lotion to the skin having the skin condition. Preferably, the lotion has a 2-hour mean blanching score of at least about 2.1, an AUC of at least about 26.7, and an average mean blanching of at least about 1.5. The lotion of the present invention has the added benefit of being chemically and physically stable for at least 6 months at 40° C.

DETAILED DESCRIPTION OF THE PREFERRED EMBODIMENTS

Fluticasone or a pharmaceutically acceptable salt or ester thereof, preferably fluticasone proprionate, is present in the formulation in a concentration of from about 0.005 to 1.0 wt. % preferably 0.005 to 0.5 wt. %, and more preferably about 0.005 to about 0.1 wt. %. The $C_{14}$-$C_{20}$ fatty alcohol or mixtures thereof are present in the formulation as a thickener and/or stabilizer. Examples include, but are not limited to, cetyl alcohol, stearyl alcohol, and cetostearyl alcohol. The $C_{14}$-$C_{20}$ fatty alcohol is present in a concentration in the range of from about 1.0 to 10.0 wt. %, preferably about 3.0 to 7.0 wt. %, and more preferably about 4.0 to 6.0 wt. %.

Conventional skin conditioning agents, such as emollient skin conditioning agents, may be present in the lotion of the present invention. Skin conditioning agents are defined in the CTFA (Cosmetic Toiletry and Fragrance Association) Cosmetic Ingredient Handbook (2nd ed. 1992) and the Handbook of Pharmaceutical Excipients (2nd ed. 1994). Preferred examples of such skin conditioning agents include, but are not limited to, cholesterol, glycerine, glycerol monostearate, isopropyl myristate and palmitate, and lanolin alcohols, or mixtures thereof. Particular examples are isopropyl myristate and cetostearyl alcohol. The skin conditioning agent is present in a concentration in the range of from about 1.0 to 5.0 wt. %, preferably about 1.0 to 3.0 wt. %, and more preferably about 1.0 to 2.0 wt. %. In a preferred embodiment, dimethicone is employed in connection with at least one skin conditioning agent. The concentration of dimethicone in the formulation may be up to about 5.0 wt. %, preferably about 0.5 to 3.0 wt. % and more preferably about 1.0 to 2.0 wt. % of the lotion composition.

At least one conventional surfactants may be used in topical formulations to form the oil-in-water emulsion lotion of the present invention. For example, the surfactants may include, but are not limited to, polyoxyalkene oxides of $C_{14}$-$C_{20}$ fatty alcohols and polyoxyalkylene sorbitan esters, or mixtures thereof. Preferred surfactants include CETOMACROGOL® 1000 (Crodor Inc.), CETETH-20®, TWEEN® 40 or BRIG® 78. The surfactant may be present in a concentration in the range of about 0.25 to 3.0 wt. %, preferably about 0.5 to 2.0 wt. %, and more preferably about 0.75 to 1.5 wt. %.

Optionally, mineral oil or white soft paraffin are incorporated into the lotion in relatively small amounts to act as a skin conditioner. The lotion may also be free of mineral oil and/or white soft paraffin or contain up to about 10.0 wt. %. The lotion may also contain up to about 5.0 wt. % or up to about 2.0 wt. % skin conditioner.

Propylene glycol may be present in the lotion formulation in a concentration of from about 5.0 to 15.0 wt. %, preferably about 7.0 to 12.0 wt. % and more preferably 9.0 to 11.0 wt. %.

The viscosity of the fluticasone lotion may be in the range of about 2,000 to 17,000 centipoise (cps), and preferably about 3,000 to 13,000 cps, as measured by a Brookfield viscometer fitted with a #27 spindle at 10 rpm at 25° C.

The pH range of the topical fluticasone lotion may be in the range of about 4 to 7. Conventional buffers may be employed in the lotion formulation to achieve the pH range. The buffers include, but are not limited to, sodium citrate/citric acid, dibasic sodium phosphate/citric acid, and the like.

Optionally, conventional preservatives may be used in the present invention. Preferably, preservatives employed in the formulation should pass US Pharmacopoeia, British Pharmacopoeia and European Pharmacopoeia standards. Preferred preservatives include, but are not limited to, imidurea, methylparaben, propylparaben and the like, and combinations thereof.

Treatment of skin conditions with the lotion of the present invention is accomplished by applying the lotion to the affected areas to be treated. The treatment regimen is varied from patient to patient and condition to condition. In general, the fluticasone lotion is to be applied once or twice a day to a treatment area. Preferably, the lotion of the present invention is used to treat atopic dermatitis, inflammatory and pruritic manifestations and corticosteroid-responsive dermatoses.

The lotion of the present invention is manufactured in a conventional manner by mixing the ingredients at elevated temperatures (such as from 45-80° C.) and then cooling the mixture to achieve a smooth, homogeneous oil-in-water emulsion.

The following examples merely illustrate the lotion compositions of the invention and are not to be construed as limiting the scope of the invention. Unless indicated otherwise, all weight percentages are based on the total weight of the composition.

EXAMPLES

Example 1

A topical 0.05 wt. % fluticasone propionate lotion in accordance with the present invention was prepared having the following composition.

| Ingredient | (wt. %) |
| --- | --- |
| Cetostearyl alcohol, NF | 5.00 |
| Isopropyl myristate, NF | 1.00 |
| Dimethicone 360, NF | 1.00 |
| Cetomacrogol 1000, BP | 1.00 |
| Propylene glycol, USP | 10.00 |
| Imidurea, NF | 0.30 |
| Methyl paraben, USP | 0.20 |
| Propyl paraben, USP | 0.10 |
| Citric acid (anhydrous), USP | 0.05 |
| Sodium citrate, USP | 0.08 |
| Purified water, USP | balance |

Example 2

A topical 0.05 wt. % fluticasone propionate lotion formulation in accordance with the present invention was prepared having the following composition.

| Ingredient | (wt. %) |
| --- | --- |
| Cetostearyl alcohol, NF | 5.25 |
| Isopropyl myristate, NF | 2.00 |
| Propylene glycol, USP | 0.00 |
| Ceteth-20 | 0.75 |
| Imidurea, NF | 0.20 |
| Methyl paraben, USP | 0.20 |
| Propyl paraben, USP | 0.10 |
| Citric Acid (anhydrous) | 0.05 |
| Dibasic sodium phosphate | 0.06 |
| Purified water, USP | balance |

Example 3

A topical fluticasone propionate lotion in accordance with the present invention was prepared having the following composition.

| Ingredient | (wt. %) |
| --- | --- |
| Fluticasone Propionate | 0.05 |
| Cetosteoryl Alcohol | 5.0 |
| Mineral Oil | 3.0 |
| Isopropyl myristate | 3.0 |
| Ceteth-20 | 0.75 |
| Propylene Glycol | 0.0 |
| Citric Acid (anhydrous) | 0.05 |
| Dibasic Sodium Phosphate | 0.06 |
| Imidurea | 0.20 |
| Water | balance |

Example 4

A topical fluticasone propionate lotion in accordance with the present invention was prepared having the following composition.

| Ingredient | (wt. %) |
| --- | --- |
| Fluticasone Propionate | 0.05 |
| Cetosteoryl Alcohol | 5.25 |

-continued

| Ingredient | (wt. %) |
|---|---|
| Mineral Oil | 1.0 |
| Isopropyl myristate | 1.0 |
| Ceteth-20 | 0.75 |
| Propylene Glycol | 10.0 |
| Citric Acid (anhydrous) | 0.05 |
| Dibasic Sodium Phosphate | 0.06 |
| Imidurea | 0.20 |
| Water | balance |

Example 5

A topical fluticasone propionate lotion in accordance with the present invention was prepared having the following composition.

| Ingredient | (wt. %) |
|---|---|
| Fluticasone Propionate | 0.05 |
| Cetosteoryl Alcohol | 5.0 |
| Mineral Oil | 10.0 |
| Isopropyl myristate | 5.0 |
| Ceteth-20 | 0.75 |
| Propylene Glycol | 10.0 |
| Citric Acid (anhydrous) | 0.05 |
| Dibasic Sodium Phosphate | 0.06 |
| Imidurea | 0.20 |
| Water | balance |

Example 6

A topical fluticasone propionate lotion in accordance with the present invention was prepared having the following composition.

| Ingredient | (wt. %) |
|---|---|
| Fluticasone Propionate | 0.05 |
| Cetosteoryl Alcohol | 7.0 |
| Isopropyl myristate | 2.5 |
| Dimethicone | 2.5 |
| Cetomacrogol 1000 | 1.0 |
| Propylene Glycol | 10.0 |
| Citric Acid (anhydrous) | 0.05 |
| Sodium Citrate | 0.075 |
| Imidurea | 0.30 |
| Water | balance |

Example 7

A topical fluticasone propionate lotion in accordance with the present invention was prepared having the following composition.

| Ingredient | (wt. %) |
|---|---|
| Fluticasone Propionate | 0.05 |
| Cetosteoryl Alcohol | 7.0 |
| Isopropyl myristate | 5.0 |
| Dimethicone | 2.5 |
| Cetomacrogol 1000 | 1.0 |
| Propylene Glycol | 10.0 |
| Citric Acid (anhydrous) | 0.05 |
| Sodium Citrate | 0.075 |
| Imidurea | 0.30 |
| Water | balance |

Example 8

A topical fluticasone propionate lotion in accordance with the present invention was prepared having the following composition.

| Ingredient | (wt. %) |
|---|---|
| Fluticasone Propionate | 0.05 |
| Cetosteoryl Alcohol | 6.0 |
| Isopropyl myristate | 2.0 |
| Cetomacrogol 1000 | 1.0 |
| Propylene Glycol | 10.0 |
| Citric Acid (anhydrous) | 0.05 |
| Sodium Citrate | 0.075 |
| Imidurea | 0.30 |
| Water | balance |

Example 9

A topical fluticasone propionate lotion in accordance with the present invention was prepared having the following composition.

| Ingredient | (wt. %) |
|---|---|
| Fluticasone Propionate | 0.05 |
| Cetosteoryl Alcohol | 4.7 |
| Isopropyl myristate | 3.75 |
| Dimethicone | 3.75 |
| Cetomacrogol 1000 | 1.0 |
| Propylene Glycol | 10.0 |
| Citric Acid (anhydrous) | 0.05 |
| Sodium Citrate | 0.075 |
| Imidurea | 0.30 |
| Water | balance |

Example 10

A topical fluticasone propionate lotion in accordance with the present invention was prepared having the following composition.

| Ingredient | (wt. %) |
|---|---|
| Fluticasone Propionate | 0.05 |
| Cetosteoryl Alcohol | 2.4 |
| Isopropyl myristate | 2.5 |
| Dimethicone | 5.0 |
| Cetomacrogol 1000 | 1.0 |
| Propylene Glycol | 10.0 |
| Citric Acid (anhydrous) | 0.05 |
| Sodium Citrate | 0.075 |
| Imidurea | 0.30 |
| Water | balance |

Example 11

A topical fluticasone propionate lotion in accordance with the present invention is prepared having the following composition.

| Ingredient | (wt. %) |
| --- | --- |
| Fluticasone Propionate | 0.01 |
| Stearyl Alcohol | 5.0 |
| Isopropyl myristate | 3.0 |
| Dimethicone | 3.0 |
| Ceteth-20 | 0.75 |
| Propylene Glycol | 5.0 |
| Imidurea, NF | 0.20 |
| Methyl paraben, USP | 0.20 |
| Propyl paraben, USP | 0.10 |
| Water | balance |

Example 12

A topical fluticasone propionate lotion in accordance with the present invention was prepared having the following composition.

| Ingredient | (wt. %) |
| --- | --- |
| Fluticasone Propionate | 0.01 |
| Stearyl Alcohol | 2.5 |
| Mineral Oil | 1.0 |
| Isopropyl myristate | 1.0 |
| Dimethicone | 1.0 |
| Cetomacrogol 1000 | 0.5 |
| Propylene Glycol | 15.0 |
| Imidurea, NF | 0.20 |
| Methyl paraben, USP | 0.20 |
| Propyl paraben, USP | 0.10 |
| Water | balance |

Example 13

A topical fluticasone propionate lotion in accordance with the present invention was prepared having the following composition.

| Ingredient | (wt. %) |
| --- | --- |
| Fluticasone Propionate | 0.1 |
| Cetyl Alcohol | 7.0 |
| Mineral Oil | 2.0 |
| Isopropyl myristate | 2.0 |
| Dimethicone | 2.0 |
| Cetomacrogol 1000 | 1.5 |
| Propylene Glycol | 10.0 |
| Imidurea, NF | 0.20 |
| Methyl paraben, USP | 0.20 |
| Propyl paraben, USP | 0.10 |
| Water | balance |

Example 14

A topical fluticasone propionate lotion in accordance with the present invention was prepared having the following composition.

| Ingredient | (wt. %) |
| --- | --- |
| Fluticasone Propionate | 0.1 |
| Stearyl Alcohol | 7.0 |
| Mineral Oil | 2.5 |
| Dimethicone | 2.5 |
| Ceteth-20 | 1.0 |
| Propylene Glycol | 15.0 |
| Imidurea, NF | 0.20 |
| Methyl paraben, USP | 0.20 |
| Propyl paraben, USP | 0.10 |
| Water | balance |

Example 15

A topical fluticasone propionate lotion in accordance with the present invention was prepared having the following composition.

| Ingredient | (wt. %) |
| --- | --- |
| Fluticasone Propionate | 0.1 |
| Cetostearyl Alcohol | 5.0 |
| Mineral Oil | 2.5 |
| Dimethicone | 1.0 |
| Tween ® 40 | 0.5 |
| Propylene Glycol | 10.0 |
| Imidurea, NF | 0.20 |
| Methyl paraben, USP | 0.20 |
| Propyl paraben, USP | 0.10 |
| Water | balance |

Example 16

A topical fluticasone propionate lotion in accordance with the present invention was prepared having the following composition.

| Ingredient | (wt. %) |
| --- | --- |
| Fluticasone Propionate | 0.1 |
| Stearyl Alcohol | 5.25 |
| Mineral Oil | 5.0 |
| Brig ® 78 | 2.0 |
| Propylene Glycol | 5.0 |
| Imidurea, NF | 0.20 |
| Methyl paraben, USP | 0.20 |
| Propyl paraben, USP | 0.10 |
| Water | balance |

Example 17

A topical fluticasone propionate lotion in accordance with the present invention was prepared having the following composition.

| Ingredient | (wt. %) |
| --- | --- |
| Fluticasone Propionate | 0.05 |
| Cetyl Alcohol | 2.0 |
| Isopropyl myristate | 5.0 |
| Cetomacrogol 1000 | 0.5 |

-continued

| Ingredient | (wt. %) |
|---|---|
| Propylene Glycol | 10.0 |
| Imidurea, NF | 0.20 |
| Methyl paraben, USP | 0.20 |
| Propyl paraben, USP | 0.10 |
| Water | balance |

Example 18

A topical fluticasone propionate lotion in accordance with the present invention was prepared having the following composition.

| Ingredient | (wt. %) |
|---|---|
| Fluticasone Propionate | 0.05 |
| Cetyl Alcohol | 2.5 |
| Dimethicone | 5.0 |
| Cetomacrogol 1000 | 1.0 |
| Propylene Glycol | 10.0 |
| Imidurea, NF | 0.20 |
| Methyl paraben, USP | 0.20 |
| Propyl paraben, USP | 0.10 |
| Water | balance |

The topical anti-inflammatory activity of fluticasone propionate formulations was measured using a vasoconstriction assay (McKenzie and Stoughton, Arch. Dermatol., 86, 608 (1962)).

Approximately 0.1 mL of the drug product of Examples 1-18 were placed on a 2 $cm^2$ area of the volar aspect of each volunteer's forearm. Application sites were protected with a guard to prevent removal or smearing. The application sites were not occluded. After approximately 16 hours of contact, the protective guards were removed and the sites gently washed and dried.

Skin vasoconstrictor evaluations were preformed on a 4 point scale (0 [no blanching]-3[marked blanching]) at time points corresponding to 2, 3, 6, 8, and 24 hours after drug removal. The data were used to calculate the mean blanching response and the area under the curve (AUC) for the blanching versus time. The higher the score, mean or area under the curve (AUC), the more topically potent. The results are tabulated in Table 1.

TABLE 1

| Measure* | Lotion Example 1 | Lotion Example 2 | CUTIVATE ® (Fluticasone proprionate) Cream Comparative Example |
|---|---|---|---|
| AUC | 28.4 | 26.7 | 21.4 |
| Mean | 1.58 | 1.49 | 1.22 |

*Results from 17 volunteers.

The fluticasone lotions of the present invention show higher vasoconstriction scores than fluticasone cream. As shown by the 17 patient data set, the vasoconstriction potency of the fluticasone lotions is greater than the cream.

The fluticasone lotion of the present invention has proven to be unexpectedly superior in terms of efficacy and safety. Evaluations were performed using the Vasoconstrictor Assay. Evaluations also used a human model to predict clinical potency of corticosteroids in (1) controlled efficacy and safety trials and (2) subjects with a corticosteroid-responsive dermatosis, atopic dermatitis. Safety and efficacy evaluations were performed on the fluticasone lotion 0.05% by applying the lotion extensively to all body regions: head and neck (including face), trunk, upper limbs and lower limbs.

The potency of the fluticasone lotion, as determined by the Vasoconstrictor Assay, was greater than mid-potency fluticasone cream (CUTIVATE™ Cream). The potency of the fluticasone lotion was less than the high-potency corticosteroid preparations. Application of the lotion formulation over 4 weeks resulted in a superior adverse event profile devoid of commonly encountered side effects encountered using corticosteroids in the mid-to-high potency range.

The instant fluticasone lotion was assessed in view of projected efficacy outcomes from the Vasoconstrictor Assay (VC Assay) in humans and corroborated by efficacy outcomes in multicenter vehicle-controlled clinical trials. It was highly desirable for the lotion formulation to show both systemic (adrenal axis suppression) and local (atrophogenic) responses to corticosteroids. The fluticasone lotion was unexpectedly superior in both categories, and particularly superior in that no atrophy was observed (based on associated signs) even in the more susceptible region (i.e., the face, head and neck).

The Vasoconstrictor Assay (VC Assay; McKenzie and Stoughton) is a standard dermatological assay used to predict the potency of corticosteroid formulations. Potency is related to both side effect potential and efficacy in the treatment of mild to severe dermatoses. Reactions of particular concern include skin thinning (atrophy, including telangectasia), and adrenal axis suppression, which can occur more often (1) under occlusions or (2) when higher potency corticosteroids are employed.

In the VC assay, fluticasone lotion 0.05% was compared to low-potency (HYTONE™ Lotion), mid-potency (CUTIVATE™ Cream; and fluticasone cream 0.05%) and high-potency (TEMOVATE™ Cream; ELOCON™ Lotion). Potency was estimated for two subject populations (Intent to Treat and Positive responders) and includes 3 outcome assessments: 2-hour mean blanching score, are under the time-blanching score curve (AUC) and Average mean blanching from 5 timepoints. The results from the "responder" population is summarised in Table 2.

TABLE 2

| | | Responder Population | | |
|---|---|---|---|---|
| Treatment | Potency | 2 hour score | AUC | Avg. mean blanching |
| TEMOVATE ™ | High | 2.7 | 36.6 | 2.0 |
| ELOCON ™ | High | 2.2 | 33.4 | 1.8 |
| Fluticasone lotion (0.05%) | Mid to High | 2.1 | 26.7 | 1.5 |
| CUTIVATE ™ Cream | Mid | 1.8 | 21.4 | 1.2 |
| HYTONE ™ Lotion | Low | 0.8 | 9.5 | 0.6 |

The results show that the fluticasone lotion of the present invention has an unexpectedly high potency for a lotion-based composition.

In addition, as shown in Table 3, criticality for the presence of fluticasone in the lotion of the present invention was established by the comparison between applying the vehicle alone (the fluticasone lotion minus the fluticasone propionate) and the fluticasone lotion. The FPL10005, FPL3003 and FPL30004 studies used the following fluticasone 0.05% lotion formulation.

| Ingredient | (wt. %) |
|---|---|
| fluticasone propionate (micronized) | 0.05 |
| cetostearyl alcohol, NF | 5.0 |
| isopropyl myristate, NF | 1.0 |
| dimethicone 360, NF | 1.0 |
| polyoxyethylene (20) cetostearyl ether, NF | 1.0 |
| propylene glycol, USP | 10.0 |
| imidurea, NF | 0.14 |
| methylparaben, NF | 0.17 |
| propylparaben, NF | 0.06 |
| citric acid (hydrous), USP | 0.05 |
| sodium citrate, USP | 0.08 |
| purified water, USP | balance (also QSAD) |

TABLE 3

| Study | Diagnosis | Application | No. subjects | Outcome Good to cleared (%) |
|---|---|---|---|---|
| FPL30003 | Atopic Dermatitis | QD for up to 4 weeks | FPL (110) Veh. (110) | FPL (78%)* Veh. (33%) |
| FPL30004 | Atopic Dermatitis | QD for up to 4 weeks | FPL (111) Veh. (107) | FPL (68%)* Veh. (28%) |

*subjects showing >50% clearing of lesions
"Veh." is vehicle only formulation

The data of Table 3 show that the fluticasone lotion is more than twice as effective as the vehicle. In a once-a-day application, the differences (%) between the vehicle-only and the fluticasone lotion are 40% and 45% (FPL30004 and FPL30003, respectively). The advantage of the fluticasone propionate lotion over the vehicle control was unexpectedly superior. It is worth noting that the fluticasone lotion application rate was half the preferred application rate of twice per day.

Systemic safety of fluticasone lotion (study FPL10005) was assessed utilising the measurement of adrenal responsiveness to a challenge of cosyntropin ($ACTH_{1-29}$) and measuring the plasma levels of cortisol both before and 30 minutes after ACTH challenge. HPA axis was considered suppressed if the cortisol response to the challenge was less than 18 ug/dL. These studies were conducted in paediatric populations from 3 months to 5 years of age. Because children have a high ratio of body mass to surface, that population is considered to be more at risk than adults.

In these studies fluticasone formulations were tested following a 3 or 4 week course of twice daily application of the fluticasone lotion to at least 35% of the body surface area in subjects with moderate to severe eczema. The results are summarised in Table 4.

TABLE 4

Cortisol responses - plasma levels = 18 ug/dL indicate suppression

| Study | Preparation | Adrenal Responsiveness, # suppressed/total |
|---|---|---|
| FPL10005 | Lotion | 0/42 |

These data show that the fluticasone lotion did not suppress the adrenal responsiveness to ACTH stimulation. CUTIVATE™ lotion produced low adrenal suppression as evaluated by the cosyntropin ($ACTH_{1-29}$) stimulation test in paediatric subjects. This age group would be expected to be the most susceptible to side effects of corticosteroids. No adrenal suppression was noted for CUTIVATE™ lotion. These results were unexpectedly superior based on potency estimates from the VC Assay.

Treating skin diseases with topical corticosteroids is of particular concern where the skin is thin (e.g., the face) due to the potential atrophy side effect. Skin atrophy and atrophy-associated signs (such as telangectasia) were monitored in safety studies (HPA Axis Suppression) and efficacy (multicenter pivotal trials). The fluticasone lotion showed no atrophy-associated changes (see Table 4). In addition, atrophogenic potential was assessed in two large multicenter trials (FPL30003, N=110 treated with fluticasone); FPL30004; N=111 treated with fluticasone). The subjects had moderate-to-severe atopic dermatitis. After once daily administration for up to 4 weeks, no atrophy or associated signs were ascribed to drug treatment.

Based on the observed outcomes in the VC Assay (used to predict clinical potency), it was expected (1) that the therapeutic benefit would be only slightly more than that for CUTIVATE™ Cream and (2) that the side effects would reflect those observed for CUTIVATE™ Cream. The results were unexpected in that the lotion formulation was more effective than, and superior to, the cream. At half the application rate of fluticasone lotion, a lack of side effects were observed. That observation was unexpected since application of steroids of similar potency typically cause some side effects. As noted herein for the lotion, the lack of both systemic (HPA Axis suppression) and local side effects, even to sensitive areas such as the face (head and neck region) was unexpected.

It will be apparent to those skilled in the art that many modifications and equivalents thereof may be made without departing from the spirit and scope of the invention as set forth in the appended claims.

We claim:

1. A topical lotion, comprising:
    about 0.005 to 1.0 wt. % fluticasone, or a pharmaceutically acceptable salt or ester thereof;
    about 4.0 to 6.0 wt. % of a $C_{14}$-$C_{20}$ fatty alcohol or mixtures thereof;
    about 1.0 to 5.0 wt. % of at least one first skin conditioning agent;
    about 5.0 to 15.0 wt. % propylene glycol; and
    the balance in water;
    wherein the lotion is free of mineral oil and white soft paraffin, and
    wherein the lotion causes more vasoconstriction when applied to living human skin than does application of a cream containing mineral oil or soft white paraffin, or both, the cream containing the same amount of the fluticasone or the pharmaceutically acceptable salt or ester thereof.

2. The lotion of claim 1 further comprising about 0.25 to 3.0 wt. % of at least one surfactant.

3. The lotion of claim 1 further comprising about 0.5 to 2.0 wt. % of at least one surfactant.

4. The lotion of claim 1 further comprising dimethicone in an amount up to about 5.0 wt. %.

5. The lotion of claim 4 further comprising about 0.5 to 3.0 wt. % of dimethicone.

6. The lotion of claim 4 further comprising about 1.0 to 2.0 wt. % of dimethicone.

7. The lotion of claim 5 wherein said $C_{14}$-$C_{20}$ fatty alcohol or mixtures thereof is cetostearyl alcohol.

8. The lotion of claim 7 wherein said first skin conditioning agent is isopropyl myristate.

9. The lotion of claim 8 further comprising about 0.25 to 3.0 wt. % of at least one surfactant.

10. The lotion of claim 8 further comprising about 0.5 to 2.0 wt. % of at least one surfactant.

11. The lotion of claim 10 wherein said surfactant is Cetomacrogol.

12. The lotion of claim 11 further comprising one or more buffers.

13. The lotion of claim 12 further comprising one or more preservatives.

14. The lotion of claim 13 wherein said fluticasone, or a pharmaceutically acceptable salt or ester thereof is fluticasone propionate.

15. The lotion of claim 14 wherein said one or more buffer is selected from the group consisting of: sodium citrate and citric acid.

16. The lotion of claim 15 wherein said one or more preservative is selected from the group consisting of: imidurea, methylparaben, and propylparaben.

17. A method of treating a skin condition treatable by fluticasone, comprising topically administering to a patient in need thereof a lotion according to claim 14.

18. The method of claim 15 wherein said skin condition is selected from the group consisting of: corticosteroid-responsive dermatosis, atopic dermatitis, inflammation, eczema, erythema, papulation, scaling, erosion, oozing, crusting and pruritis.

19. A topical lotion, comprising:
  about 0.05 wt. % fluticasone, or a pharmaceutically acceptable salt or ester thereof;
  about 4.0 to 6.0 wt. % of cetostearyl alcohol;
  about 1.0 to 2.0 wt. % of isopropyl myristate;
  about 5.0 to 15.0 wt. % propylene glycol;
  about 0.5 to 3.0 wt. % of dimethicone;
  about 0.25 to 3.0 wt. % of at least one surfactant; and
  the balance in water;
  wherein the lotion is free of mineral oil and white soft paraffin, and
  wherein the lotion causes more vasoconstriction when applied to living human skin than does application of a cream containing mineral oil or soft white paraffin, or both, the cream containing the same amount of the fluticasone or the pharmaceutically acceptable salt or ester thereof.

* * * * *